US006365173B1

(12) United States Patent
Domb et al.

(10) Patent No.: US 6,365,173 B1
(45) Date of Patent: Apr. 2, 2002

(54) STEREOCOMPLEX POLYMERIC CARRIERS FOR DRUG DELIVERY

(75) Inventors: Abraham J. Domb, Efrat; Zeev Zehavi, Kochav-Yair, both of (IL)

(73) Assignee: Efrat Biopolymers Ltd., Efrat (IL)

( * ) Notice: Subject to any disclaimer, the term of this patent is extended or adjusted under 35 U.S.C. 154(b) by 0 days.

(21) Appl. No.: 09/231,552

(22) Filed: Jan. 14, 1999

(51) Int. Cl.[7] .......................... A61F 2/00; A61F 13/00; A61K 9/22; A61K 9/14
(52) U.S. Cl. .................. 424/426; 424/422; 424/468; 424/484; 424/486; 514/944; 514/969
(58) Field of Search .................... 424/422, 426, 424/468, 484, 486; 514/944, 969

(56) References Cited

U.S. PATENT DOCUMENTS

| | | |
|---|---|---|
| 4,719,246 A | 1/1988 | Murdoch et al. |
| 4,766,182 A | 8/1988 | Murdoch et al. |
| 4,767,628 A | 8/1988 | Hutchinson |
| 4,800,219 A | 1/1989 | Murdoch et al. |
| 4,902,515 A | 2/1990 | Loomis et al. |
| 4,981,696 A | 1/1991 | Loomis et al. |
| 5,053,485 A | 10/1991 | Nieuwenhuis et al. |
| 5,100,669 A | 3/1992 | Hyon et al. |
| 5,270,400 A | 12/1993 | Spinu |
| 5,290,494 A | 3/1994 | Coombes et al. |
| 5,317,064 A | 5/1994 | Spinu |
| 5,346,966 A | 9/1994 | Spinu |
| 5,397,572 A | 3/1995 | Coombes et al. |
| 5,578,325 A | 11/1996 | Domb et al. |
| 5,650,173 A | 7/1997 | Ramstack et al. |
| 5,725,881 A | 3/1998 | Buchholz et al. |

FOREIGN PATENT DOCUMENTS

| | | |
|---|---|---|
| EP | 0 330 180 A1 | 8/1989 |
| EP | 0 438 426 B1 | 11/1993 |
| WO | WO 97/02810 | 1/1997 |

OTHER PUBLICATIONS

Sustained Release Medications Ed. J.C. Johnson pp. 30–33, 1980.*
Barrera, et al., "Synthesis and RGD Peptide Modification of a New Biodegradable Copolymer: Poly(lactic acid–co–l–ysine)," *JACS* 115:11010–11011 (1993).
Brizzolara, et al., "Mechanism of the Stereocomplex Formation between Enantiomeric Poly(lactide)s," *Macromolecules* 29:191–197 (1996).
Crämer, et al., "Atomic force microscopy of polyethylene and poly–(D–lactide) single crystals," *Polymer Bulletin* 35:457–464 (1995).
Domb, et al, *Handbook of Biodegradable Polymers*, Harwood Academic Publishers: Amsetrdam, 1997.
Domb, et al., "Polyanhydrides. I. Preparation of High Molecular Weight Polyanhydrides," *J. Poly. Sci.* 25:3373–3386 (1987).
Duddu, et al., "Stereoselective dissolution of propranolol hydrochloride from hydroxypropyl methylcellulose matrices," *Pharm Res.* 10(11):1648–53 (1993).
Gref, et al., "The controlled intravenous delivery of drugs using PEG–coated sterically stabilized nanospheres," *Advanced Drug Delivery Reviews* 16:215–233 (1995).
Gref, et al., "Poly(ethylene glycol)–Coated Nanospheres: Potential Carriers for Intravenous Drug Administration" in *Protein Delivery–Physical Systems*, L. M. Sanders and H. Hendren, Eds, Chap. 6, Plenum Press, (1997).
Jeong, et al., "Biodegradable block copolymers as injectable drug–delivery systems," *Nature* 388(6645):860–2 (1997).
Spinu, et al., "Material design in poly(lactic acid) systems: block copolymers, star homo– and copolymers, and stereocomplexes," *J.M.S.–Pure Appl. Chem.* A33(10):1497–1530 (1996).
Ye, et al., "Bioresorbable microporous stents deliver recombinant adenovirus gene transfer vectors to the arterial wall," *Ann Biomed Eng.* 26(3):398–408 (1998).
Zhang & Eisenberg, "Multiple Morphologies of "Crew–Cut" Aggregates of Polystyrene–b–poly(acrylic acid) Block Copolymers," *Science* 268:1728–1731 (1995).

* cited by examiner

Primary Examiner—Thurman K. Page
Assistant Examiner—Humera N. Sheikh
(74) *Attorney, Agent, or Firm*—Holland & Knight LLP

(57) ABSTRACT

A polymeric carrier for delivery of bioactive or bioreactive molecules is provided, including a stereocomplex of one or more biocompatible polymers and having incorporated on or within the complex the molecules to be delivered. In a preferred embodiment, the biocompatible stereoselective polymers are linear or branched D-PLA homo- and block-polymers, linear or branched L-PLA homo- and block-polymers, copolymers thereof, or mixtures thereof, in stereocomplexed form. In one preferred embodiment, the polymeric carrier is complexed with a complementary stereospecific bioactive molecule. In other embodiments, the bioactive, or bioreactive (for example, for use in diagnostic applications), is bound to the complex by ionic, hydrogen, or other non-covalent binding reactions not involving stereocomplexation, or is physically entrapped within the complex, either at the time of complex formation or when the polymeric material is formulated into particles, tablets, or other form for pharmaceutical application. Exemplary bioactive molecules include peptides, proteins, nucleotides, oligonucleotides, sugars, carbohydrates, and other synthetic or natural organic molecules, as well as stereoselective drugs of a molecular weight of 300 daltons or higher. Examples demonstrate preparation of stereocomplexes, as well as their use for controlled and/or sustained release.

20 Claims, No Drawings

STEREOCOMPLEX POLYMERIC CARRIERS FOR DRUG DELIVERY

FIELD OF THE INVENTION

The present invention relates to a carrier formed of stereocomplexes of polymers for delivery of bioactive or bioreactive molecules.

CROSS REFERENCE TO RELATED APPLICATION

Priority is claimed to Israeli patent application Serial No. 122933, filed on Jan. 14, 1998.

BACKGROUND OF THE INVENTION

Much research has focused on the development of materials which are biocompatible and degrade chemically or enzymatically in vivo to inert or normal metabolites of the body. The preferred material degrades completely in vivo so there is no need to remove the device at the end of treatment. Direct implantation of a drug loaded device is particularly useful for drugs that undergo first pass metabolism. Linear polyesters of lactide and glycolide have been used for more than three decades for a variety of medical applications, including delivery of drugs. Handbook of Biodegradable Polymers, A. Domb, J. Kost and D. Wiseman, Harwood and Brooks (1997). Extensive research has been devoted to the use of these polymers as carriers for controlled drug delivery of a wide range of bioactive agents for human and animal use. Injectable formulations containing microspheres of lactide/glycolide polymers have received the most attention in recent years.

Polymer characteristics are affected by the monomer types and composition, the polymer architecture, and the molecular weight. The crystallinity of the polymer, an important factor in polymer biodegradation, varies with the stereoregularity of the polymer. For example, racemic D,L poly(lactide) or poly(glycolide) is less crystalline than the D or L homopolymers. Poly(lactide) (PLA) and its copolymers having less than 50% glycolic acid content are soluble in common solvents such as chlorinated hydrocarbons, tetrahydrofuran, and ethyl acetate while poly(glycolide) (PGA) is insoluble in common solvents but is soluble in hexafluoroisopropanol.

PLA has wide applications in medicine because of its biocompatibility and degradability to nontoxic products. Micelles and particles of the AB block copolymer poly (lactide)-b-poly(ethyleneglycol) (PLA-b-PEG) have received attention for use in intravenous injectable delivery systems for extended and target drug release. Gref, R. et al., Protein Delivery-Physical Systems, L. M. Sanders and H. Hendren, Eds, Plenum Press, (1997); and Gref, R. et al., Advanced Drug Delivery Reviews, 16: 215–233 (1995). Similarly, U.S. Pat. No. 5,578,325 to Domb et al. teaches multiblock copolymers comprising a multifunctional compound covalently linked with one or more hydrophilic polymers and one or more hydrophobic bioerodible polymers and including at least three polymer blocks. A PEG-coating on a microparticle or other polymeric device prevents the adsorption of plasma proteins and fast elimination by the reticulo endothelial system (RES). Possible applications for this kind of pharmaceutical depot devices are the delivery of drugs with short half-lives, transport of contrast agents, chemotherapy, and gene therapy.

AB-block copolymers of poly(styrene)-b-poly(acrylic acid) (PS-b-PAA) produce vesicle type particles which can be isolated from solution. Zhang, L. et al., Science (1995) 268, 1728. The vesicles have diameters up to 1 micron, which is much larger than that of a single micelle. This is explained by the irreversible formation of the vesicles by the fusion of micelles. However, once the micelles are associated, the high Tg of poly(styrene) (PS) freezes the structure since the PS-blocks are no longer in equilibrium with the solvent and the structure is still stable after removing the solvent. Vesicular architecture of block copolymers would appear to offer future opportunities for pharmaceutical drug devices. Nevertheless, PS and PAA cannot be used as biodegradable carriers because they are stable and do not degrade in biological mediums.

There is still a great need for a safe and effective delivery systems for labile and/or large molecules such as bioactive peptides, proteins, plasmid genes and antisense molecules, to be delivered to specific targets (tissue, cells or nucleus). Present methods are ineffective and result in poor transfection yield and toxicity when the carrier is a polycation. The major problems in the delivery of peptide and proteins are due to their instability and fast release from the polymer matrix.

It would be advantageous to have better polymeric carriers for macromolecules such as peptides, proteins, and nucleic acids.

It is therefore an object of the present invention to provide novel polymer-bioactive compositions and formulations having desirable properties for controlled and/or sustained drug delivery.

It is a further object of the present invention to provide materials which can be formulated into nano- and micro-structures for use as carriers for controlled drug delivery.

It is still another object of the present invention to provide methods for use of these compositions in the selective and extended release administration of bioactive small molecules and macromolecules such as peptides, proteins, and polynucleotides (antisense and genes).

SUMMARY OF THE INVENTION

A polymeric carrier for delivery of bioactive or bioreactive molecules is provided, including a stereocomplex of one or more biocompatible polymers and having incorporated on or within the complex the molecules to be delivered. In a preferred embodiment, the biocompatible stereoselective polymers are linear or branched D-PLA homo- and block-polymers, linear or branched L-PLA homo- and block-polymers, copolymers thereof, or mixtures thereof, in stereocomplexed form. In one preferred embodiment the polymeric carrier is complexed with a complementary stereospecific bioactive molecule. In other embodiments, the bioactive, or bioreactive (for example, for use in diagnostic applications), is bound to the complex by ionic, hydrogen, or other non-covalent binding reactions not involving stereocomplexation, or is physically entrapped within the complex, either at the time of complex formation or when the polymeric material is formulated into particles, tablets, or other form for pharmaceutical application. Exemplary bioactive molecules include peptides, proteins, nucleotides, oligonucleotides, sugars, carbohydrates, and other synthetic or natural organic molecules, as well as stereoselective drugs of a molecular weight of 300 Dalton or higher.

Examples demonstrate preparation of stereocomplexes, as well as their use for controlled and/or sustained release.

DETAILED DESCRIPTION OF THE INVENTION

Stereocomplexation of macromolecules to biodegradable polymers is a new approach in the delivery of macromolecules. The interaction at the molecular level between the polymer carrier and the bioactive macromolecule provides stability, which allows for extended release and for easy access to the target cell or tissue with minimal toxicity.

The formation of stereocomplexes between enantiomorphic PLAs and blends has previously been investigated by Cramer, K. et al., Polymer Bulletin 35:457–464 (1995); Brizzolara, D. et al., J. Computer-Aided Meter. Design, 3:341–350 (1996); and Brizzolara, D. et al., Macromolecules, 29:191 (1996). Stereocomplexes including a racemic packing of enantiomorphic poly(L-lactide) [L-PLA] and poly(D-Lactide) [L-PLA] have a melting point 60° C. higher than chiral crystals with the packing of isomorphic PLA's. As a consequence of the different packing, the chiral and racemic single crystals exhibit different morphologies. The stereocomplex forms lamella triangular or rounded hedrite type crystals instead of lozenge shaped crystals.

In contrast, as described herein in the examples, PLA-b-PEG aggregates to supra molecular assemblies like flat or tubular rods of hundreds of nanometers wide and a few microns long. Powder-diffraction patterns indicate that the crystallization of both blocks are the driving force for the formation of the mesoscopic suprastructures. The crystallized blocks are not in equilibrium with the solvent for very long, which explains the stability of the structures after removing the solvent. In combination with the racemic crystallization of the PLA-blocks, vesicle type particles emerge from dioxane and acetonitrile solutions. The racemic particles of PEG-b-L-PLA/PEG-b-D-PLA should have a similar assembly to the PS-b-PAA particles. The racemic particles of PEG-b-PLA have a much higher potential as a drug carrier system because of the safety of the polymer and its degradation products. The hydrophobic content within the vesicles should support the encapsulation of non-polar drugs. The hydrophobic/hydrophilic content may provide a type of target mechanism to pass through lipid membranes.

The constitution of PLA and peptides is similar, with the exception that PLA is a polyester and peptides are polyamides. Esters cannot form hydrogen bonds to each other since they lack hydroxyl groups. In organic solvents poly (amino acids) do not form hydrogen bonds. Thus the crystallization and packing of poly(amino acids) is comparable to PLA. Enantiomorphic poly(alanine) and PLA were crystallized into a racemic lattice to better understand the specific interactions between peptides and synthetic polymers. Until now only microparticles of the statistical copolymer poly(lactide)-b-poly(glycolide) containing LHRH showed the delayed liberation of the hormone. The specific interactions between the polymer and LHRH is the reason for the strong adhesion to the polymer matrix. A deeper understanding of the kind of interactions between peptides and polymers is necessary so that other peptides which can be encapsulated effectively, like LHRH, can be identified.

The initial results from force field simulation are promising. They demonstrate that the interaction energy between enantiomorphic poly(alanine) and PLA is greater than between isomorphic PLA. Based on the force-field calculation results, the racemic crystallization between poly (alanine) and PLA is favored compared to the separate crystallization.

I. Polymeric Carriers

Polymers

Polymeric carriers are provided for delivery of bioactive or bioreactive molecules, which include at least one biocompatible stereoselective polymer. Examples of useful polymers include polyhydroxy acids, polyhydroxyalkyls, polyalkylene oxides, polyesters, polycarbonates, and polyanhydrides. In a preferred embodiment, the carrier is formed from linear or branched D-PLA homo- or block-polymers, linear or branched L-PLA homo- or block-polymers, copolymers thereof and mixtures thereof where the copolymers are linear or branched D-PLA or L-PLA block copolymer copolymerized with a component such as a poly(hydroxyalkyl acid), polycarbonate or polyanhydride.

Polymeric carriers can also be formed of, or include, a stereocomplex of homo- or block-copolymers of D-lactide or homo- or block-copolymers of L-lactide with inert polyamino acids (such as polyalanine or polylysine), polypeptides or polysaccharides. The block length of the enantiomeric segment is typically equivalent to ten lactide units or more.

Examples of proteins or polyamino acids that are particularly useful as components in stereocomplexes include albumin, gelatin, collagen, fibrinogen, polyalanine, polyglycine, and polylysine.

Polymers which are particularly useful for stereocomplexation in gene therapy are those with a stereoselective structure with cationic sites that allow a plasmid to be complexed by diasteriomer formation and by electrostatic complexation. Representative polymers are: D-PLA graft and block copolymers with short polyamine such as polyethylene imine (Mw<2,000), poly(lysine), spermine, spermidine and copolymers of D-lactide and D-lysine.

Methods for Making Polymers and Polymer Complexes

The general synthetic procedures for the synthesis of the polymers is as follows. Polymers are dissolved in a suitable solvent and appropriate polymerization catalysts such as short alcohols, polyethylene glycol (PEG), fatty alcohol or polyalcohol, added in a range such as 0.1 to 3 mole percent per lactide. The solvent is removed after polymerization is initiated, for example, by solvent evaporation The molar ratio between the monomer and the catalyst determine the polymer block molecular weight. The length and number of blocks is controlled by the number of and amount of each monomer units added and the amount of catalyst used.

Alternatively, pre-prepared polymer blocks with hydroxyl and carboxylic acid can be conjugated via an ester, phosphate, anhydride, or carbonate bond. The hydroxyl end groups are reacted with either a diacid chloride (i.e. adipoyl chloride, sebacoyl chloride), alkyl phosphodichloridate, or phosgene to form ester, phosphate or carbonate block conjugates, respectively. Anhydride copolymers are prepared by activating the PLA carboxylic acid end group with acetic anhydride and copolymerized with sebacic acid prepolymer according to Domb et al., J. Poly. Sci. 25:3373 (1987). Multiblock copolymers of PLA are prepared by using a polyalcohol such as pentaerythritol, or glycerol in the catalyst mixture. The structures and block length can be determined by H-NMR and GPC. Typical MW of polymers is in the range of 5,000 to 100,000.

For example, homopolymers of PLA were synthesized by dissolving D-lactide or L-lactide in dry toluene at 100° C. and adding a solution of stannous octoate and alcohol as polymerization catalyst (5% solution in toluene, 0.1 to 3 mole % per lactide). After 3 hours the solvent was evaporated to dryness and the viscous residue was left at 130° C. for additional 2 hours to yield the polymer. When lactide block copolymers were prepared, the first block, i.e. L-lactide, was prepared in toluene at 100° C. and a second portion of lactide, i.e. D-lactide, was added and polymerization continued for an additional 2 hours; then a third portion of lactide was added and the polymerization continued. Block copolymers with cyclic hydroxy alkyl acids and cyclic carbonates are prepared in a similar manner, but the second portion is the desired cyclic monomer (caprolactone, trimethylene carbonate, glycolide), instead of lactide.

A tetrablock copolymer consisting of two D-PLA chains and two L-PLA chains was prepared by polymerizing D-lactide with dibenzyl tartarate using stannous octoate as catalyst. After polymerization at 130° C. as described above, the benzyl protecting groups were removed by hydrolysis or hydrogenation. The free acid groups were esterified with hydroxyl terminated L-PLA in chloroform solution and DCC as coupling agent. The length of the blocks varied depending on the amount of D-lactide used for polymerization and the L-PLA chain length. This polymer formed an intra and inter-stereocomplexation. Other multiblock polymers contained blocks of either or both D-PLA and L-PLA and other biodegradable polymers or poly(oxyalkanes) or contained other branching molecules like mucic acid, pentaerythritol, citric acid and malonic acid 2-methanol.

To form stereocomplexes, polymer is either dissolved in a solvent in which the polymers are soluble or the polymer components melted together. The polymer mixture is stored under conditions at which the polymers will complex and precipitate out of solution, or cool. The mixture can be formed into a desired shape as it forms, or processed after stereocomplex formation.

Solvents which can be used to dissolve polymers for formation of stereocomplexes include dioxane, chloroform tetrahydrofuran, ethyl acetate, acetone, N-methylpyrrolidone, ethyl and methyl lactate, ethyl acetate and mixtures of these solvents, and other solvents, such as water, short chain alcohols and carboxylic acids (C5 or below). The particle size of the precipitate is controlled by the selected solvent, the drug, and polymer concentrations, and the reaction conditions (temperature, mixing, volume etc.).

As demonstrated by the following examples, a range of copolymers containing stereoselective blocks of enantiomorphic PLA were synthesized and used to form nanoscale structures resulting from specific stereocomplexations. Block copolymers containing blocks of D-lactide and L-lactide, as shown in Table 1, were synthesized. Polymer blocks of molecular weights ranging from 600 to 100,000 daltons were prepared; their molecular weights were estimated by gel permeation chromatography (GPC) and determined by 1H-NMR. L-PLA blocks of 20 to 100 lactide units were conjugated to a biodegradable polyanhydride, polycaprolactone and polyhydroxybutyrate, or to the hydrophilic poly(ethylene glycol) or poly(propylene glycol). The stereocomplexation of these copolymers with short and long chain polymers of D-lactide at different solutions and conditions was characterized by atomic force microscopy (AFM) and related surface characterization methods (SEM, TEM, XPS). The interaction of poly(D-lactide) and its copolymers with peptides and oligonucleotides to form spontaneous nanoparticles was evaluated as a delivery system to tissues or to cells. Other block copolymers of PLA, such as diblock copolymers of D-PLA-co-L-PLA were also prepared in the manner stated above, using the proper solvents.

Table 1: Structures of Block Copolymers
  a. Lactide Copolymers
    homopolymers of $(D-LA)_x$ or $(L-LA)_x$ $x=10$ to 5,000
    block copolymers of $[(D-LA)_x-X-(L-LA)_y]_z$
      where x, y=10 to 5,000 and z=0 to 100
    block copolymers of $[(DL-LA)_x-X-(L-LA)_y]_z$
      where x, y=10 to 5,000 and z=0 to 100
    block copolymers of $[(D-LA)_x-X-(DL-LA)_y]_z$
    where x, y=10 to 5,000 and z=0 to 100
    block copolymers of $[(D-LA)_x-X-(DL-LA)_y]_z$
      where x, y=10 to 5,000 and z=0 to 100
      X=ester, carbonate, ether, phosphate, anhydride, orthoester, or a branching molecule
  b. PLA-polyanhydride Copolymers
    block copolymers of $[(D-LA)_x-co-(COO—R—CO)_y]_z$
      where x, y=10 to 5,000 and z=0 to 100
      R=aliphatic, aromatic or heterocyclic residue
    block copolymers of $[(L-LA)_x-co-(COO—R—CO)_y]_z$
      where x, y=0 to 5,000 and z=0 to 100
      R=aliphatic, aromatic or heterocyclic residue
  c. PLA-poly(hydroxy Alkyl Acid) and Carbonate Copolymers
    block copolymers of $[(D-LA)_x-co-(CO—R'—O)_y]_z$
      where x, y=10 to 5,000 and z=0 to 100
      $R'=(CH_2)_{1-5}$, $CH(CH_2—CH_3)CH_2$, $O—(CH_2)_{2-3}$
    block copolymers of $[L-LA)_x-co-(CO—R'—O)_y]_z$
      where x, y=10 to 5,000 and z=0 to 100
      $R'=(CH_2)_{1-5}$, $CH(CH_2—CH_3)CH_2$, $O—(CH_2)_{2-3}$
  d. PLA-poly(ethylene and Propylene Oxides) Copolymers
    block copolymers of $[(D-LA)_x-co-(O—CH_2—CH_2)_y]_z$
      where x, y=10 to 5,000 and z=0 to 100
    block copolymers of $[(D-LA)_x-co-(O—CH_2—CH(CH_3))_y]_z$
      where x, y=10 to 5,000 and z=0 to 100
    block copolymers of $[(L-LA)_x-co-(O—CH_2—CH_2)_y]_z$
      where x, y=10 to 5,000 and z=0 to 100
    block copolymers of $[(D-LA)_x-co-(O—CH_2—CH(CH_3))_y]_z$
      where x, y=10 to 5,000 and z=0 to 100
  e. PLA Multiblock Copolymers
    multiblock copolymers $[(D-LA)_x]_a-X-[(O—CH_2—CH_2)_y]_b$
      where x, y=10 to 5,000 and a, b=1 to 6
      X=tartaric acid, mucic acid, citric acid
    multiblock copolymers $[D-LA)_x]_a-X-[L(L-LA_x]_b)$
      where x, y=10 to 5,000 and a, b=1 to 6
      X=penaerytritol mono- and polysaccharides glycerin II. Pharmaceutical Formulations Bioactive Molecules The stereocomplexes can be used to deliver any of a variety of molecules which may broadly be classed as bioactive or bioreactive molecules, for therapeutic, prophylactic or diagnostic applications, referred to generally herein as "bioactive molecules". In some cases one or more of the polymeric components of the stereocomplex will consist of the bioactive molecules. Bioactive molecules can be any of the broad chemical classes of peptides, proteins, sugars, carbohydrate, lipids, nucleotides, oligonucleotides, and combinations thereof such as glycoproteins. Examples of preferred bioactive molecules include hormones, clotting factors, proteases, growth factors; and vaccines. Examples of peptides include hormones such as LHRH, GNRH, enkephalin, ACTH, a-MSH, somatostatin, calcitonin, insulin and their analogs. Examples of proteins include erythropoeitin, t-PA, Factor VIII, growth hormone, growth factors like FGF, BMP, and EGF; and vaccines against bacterial or viral pathogens such as vaccines containing as antigens staphylococcal enterotoxin B toxoid, HGC-DT, diphtheria toxoid and ribonuclease A. Examples of preferred oligonucleotides include antisense, genes, plasmids and viral vectors.

Formulations

The bioactive molecules can be incorporated onto or into the stereocomplexes. They can be coupled to the stereocomplexes by ionic, hydrogen or other types of bond formation, including covalent bond formation. The bioactive molecules can be incorporated into the stereocomplexes when the polymers are mixed together in solution or melted, so that the molecules are entrapped within the polymer complex as it precipitates or cools. They can also physically be mixed with the stereocomplexes as these are formulated into tablets, molds, or particles, as described below. Alternatively, the bioactive molecules can be coupled to the stereocomplexes after formation of the complexes or the formulations containing the complexes.

The stereocomplexes are typically formed into devices for drug delivery using standard polymer processing techniques to form particles including nanoparticles, microspheres, and microcapsules, pellets, tablets, films, rods, or beads. Alternatively, the polymers can be formulated into a paste, ointment, cream, gel, or transdermal patch.

The polymers can also be lyophilized and then formulated into an aqueous suspension in a range of microgram/ml to 100 mg/ml prior to use. Suitable vehicles include water, saline, and phosphate buffered saline.

Administration of the Stereocomplex Formulations

The bioactive or bioreactive component can be administered once, or may be divided into a number of smaller doses to be administered at varying intervals of time, depending on the release rate of the carrier and the desired dosage. The above formulation principles are well known in the art. The formulations can be administered to a patient in a variety of routes, for example, orally, parenterally, intravenously, intradermally, subcutaneously, or topically, in liquid, cream, gel, or solid form, as appropriate for the drug to be delivered.

The carrier should contain the substance to be delivered in an amount sufficient to deliver to a patient a therapeutically effective amount of compound. The desired concentration of active compound with the carrier will depend on absorption, inactivation, and excretion rates of the drug, as well as the delivery rate of the compound from the carrier. It is to be noted that dosage values will also vary with the severity of the condition to be alleviated. It is to be further understood that, for any particular subject, specific dosage regimens should be adjusted over time according to the individual need and the professional judgment of the person administering or supervising the administration of the compositions.

The present invention is further described by the following non-limiting examples.

Methods and Materials used in the Examples

Molecular weights of polymers were estimated on gel permeation chromatography (GPC) system consisting of a Spectra Physics (Darmstadt, Germany) P1000 pump with UV detection (Applied Bioscience 759A Absorbency UV detector) at 254 nm. Samples were eluted with $CHCl_3$ through a linear Styrogel column (10 pore size) at a flow rate of 1 ml/min. Molecular weights were determined relative to polystyrene standards (Polyscience, Warrington, Pa.) with molecular weight range of 400 to 100,000 g/mol using a WINner/286 computer program. The ratio of the PEG- and PLA- blocks were determined from 1H-NMR data.

Atomic-force-Microscopy. A scanning probe microscope 'Nanoscope III' (Digital Instruments Inc.) was used. Rectangular Si cantilevers (Nano-probes) were applied for the tapping mode experiments. Simultaneous registration was performed in the tapping mode for height and amplitude images. The specimen for AFM were prepared by depositing one drop of 0.1% solution of the AB-block copolymer on mica and evaporating the solvent. Stereocomplexes of enantiomorphic PLA-blocks were prepared by mixing equimolar solutions and stirring on a low speed for 1 week.

Powder Diffraction. Powder patterns were measured on a STOE (Darmstadt, D) image plane system at a distance of 130 mm with CuKa radiation. The solutions prepared for AFM were cast onto a microscope glass and the remaining film after evaporation of the solvent was poured into a x-ray tube.

EXAMPLE 1

Formation of Stereocomplexes by Precipitation

Stereocomplexes were prepared as follows. Table 2 illustrates the differences between the melting points of homopolymers of the starting materials and the melting points of the stereocomplexes.

a. L-PLA and D-PLA in Acetonitrile

L-PLA (1 gram, Mw=30,000) and D-PLA (1 gram, Mw=30,000) were added to 70 ml of acetonitrile at 60° C. The clear solution became turbid after about 4–5 hours, and after two days at 60° C., a heavy white solid precipitated. After three days, the solution was filtered, and the stereocomplex was collected and dried in vacuum over night.

The precipitate was analyzed for particle size and shape by particle size analyzer (Coulter) and AFM. The average particle size was 2.1 microns with various particle shapes, mostly consisting of flat discs. The melting point of the complex was 234.8° C.

b. L-PLA and D-PLA in $CHCl_3$

L-PLA (0.5 g, Mw=30,000) and D-PLA (0.5 g, Mw=30,000) were dissolved in 10 ml=$CHCl_3$. After formation of a precipitate and evaporation of the solvent, essentially as described in example a, the melting point of the powder was measured to be 232° C.

c. D-PLA-PEG and L-PLA-PEG

A stereocomplex of D-PLA-PEG and L-PLA-PEG was prepared according to the procedure described in example b. The melting point was determined to be 221° C.

d. D-PLA-co-poly(sebacic anhydride) and L-PLA-co-glycolide

Diblock D-PLA-co-poly(sebacic anhydride) (0.5 g, 1:1 w/w ratio Mw 22,000) was mixed with L-PLA-co-glycolide (0.5 g, 1:1 w/w ratio Mw 24,000) in 50 ml of a mixture of acetonitrile and chloroform (9:1 v/v ratio acetonitrile: chloroform). After 24 hours at 40° C., the precipitated polymer had a melting point at 220° C., which indicates stereocomplex formation.

TABLE 2

Stereocomplexes melting points (DSC):

| Polymer | $T_m$ (° C.) |
|---|---|
| D-PLA or L-PLA enantiomer | 179.6 |
| DL-PLA racemic random polymer | amorphous |
| DL-PLA-PEG racemic random polymer | amorphous |
| D-PLA:L-PLA 1:1 ratio stereocomplex | 234.8 |
| D-PLA-PEG or L-PLA-PEG | 176.0 |
| D-PLA-PEG: 1:1 stereocomplex | 237.5 |
| L-PLA and D-PLA($CHCl_3$), | 232 |
| PLA-PEG and L-PLA-PEG($CHCl_3$). | 221 |

EXAMPLE 2

Stereocomplex Formation by Melting of L-PLA and D-PLA

L-PLA (0.5 g, Mw=30,000) and D-LPA (0.5 g, Mw=30,000) were mixed and heated at 100° C. for 2 hours and the melting point was measured by DSC. The mixture melted at two points: 176° C. (which is PLA) and 230° C. The presence of the two melting points demonstrates that melting two components together results in the formation of a stereocomplex.

EXAMPLE 3

Morphology of Stereocomplexes of D-PLA-b-PEG/ L-PLA-b-PEG Containing Bioactive Molecules When Suspended in Various Solvents Solutions of D-PLA-b-PEG and L-PLA-b-PEG (molecular weight of 7,000 and 30,000) and a hydrophilic bioactive molecule such as LHRH or albumin were mixed in aqueous buffer solution for 24 hours and the precipitate was isolated and analyzed. A variety of structures was observed. The most characteristic structures were rods and coiled coils with lengths and diameters up to several micrometers. In contrast, no differences were observed between the morphologies formed by racemic and those formed by chiral crystallized PLA-blocks in aqueous solutions. A network of rods emerged from an equimolar aqueous solution of D-PLA-b-PEG/L-PLA-b-PEG. The rods measured 90 nm by 200 nm and were flat, without exhibiting a round shape. The length of the block copolymers was 30 nm; smaller than the size of the rods. The rods or threads were similar to long crystal lamellae. The surface of the rods exhibited a regular pattern, which is likely related to a regular packing of the block copolymers inside the rods.

In dioxane solutions containing homo block copolymer or an equimolar mixture of L-PLA-b-PEG/D-PLA-b-PEG, large mesoscopic coiled coils were observed. The optical microscope and AFM image of a coiled coil showed that the dimensions (width 450 nm and height 250 nm) were smaller than the dimensions of a coiled coil formed in water solutions. The rods consist of two smaller threads which form a regular repeating coiled coil. The height data demonstrates that a coiled coil was formed, because the height is greater when the rods cross over each other.

In equimolar dioxane solutions of L-PLA-b-PEG/D-PLA-b-PEG, an additional structure developed which was not observed in solutions of homo block copolymer. These solutions developed discs. However, the dimensions of the discs formed by PEG-b-L-PLA-1/PEG-b-D-PLA-1 and PEG-b-L-PLA-2/PEG-b-D-PLA-2 are different (where 1 is low mw and 2 is high mw). AFM analysis showed that discs of PEG-b-L-PLA-1/PEG-b-D-PLA-1 had diameters between 200 nm and 3 microns and heights of between 30 and 200 nm. The center of the discs was indented. In contrast, the block copolymers PEG-b-L-PLA-2/PEG-b-D-PLA-2 formed monodisperse discs with diameters of approximately 1 mm and heights of between 90 and 120 nm. The dimensions of the discs exceeded the size of a single block copolymer micelle, which has a diameter of between 60 and 80 nm. Preparation of discs with the same dimensions and shapes was reproducible. In contrast, the rods and coiled coils emerged randomly and irregularly, with different dimensions, and in small amounts.

In acetonitrile solutions of PEG-b-L-PLA, large crystal needles and rods emerged, instead of mesoscopic coiled coils. This result likely indicates that the coiled coil structures developed from a two-dimensional, lamellae assembly in water and dioxane. Discs also emerged from acetonitrile solutions of L-PLA-b-PEG/D-PLA-b-PEG. Their average dimensions were 1.1 mm diameter and height of between 90 and 120 nm. These discs had a greater tendency to coagulate than those produced from dioxane solutions. The racemic block copolymer discs had a great similarity to disc-like crystals of the homopolymer stereocomplex. Whether crystallization forms triangular or rounded crystals depends on the crystallization conditions. The rounded crystals preferentially form from concentrated acetonitrile solutions (1%). Rounded crystals were obtained by fast cooling of a heated 0.1% acetonitrile solution.

The rounded crystals could be hedrites which are a transition from lamellae single to spherulitic crystal growth. The diameter of the hedrites was 5 microns and the height was 200 nm; further they exhibited a deep hole in the middle. The hole may be the result of a disordered nucleation, such that when the nucleus has reached a critical size, the respective sides of the crystal grow faster.

The similarity of the block copolymer and homopolymer discs demonstrates that the rounded shape of the block copolymer discs may be primarily due to the racemic packed enantiomorphic PLA-blocks.

The balance between surface free energy, dependent on the solvent and nucleation and crystal growth seem to be the key issues for understanding the differences in the structures formed from different solvents.

EXAMPLE 4

Compression Molding of Lidocaine Delivery Devices

A fine powder of the nano-discs stereocomplexed of D-PLA and L-PLA and their complexes which were of flat shapes of discs, rods, and triangles, as analyzed in Example 3, provided a unique opportunity for the preparation of drug delivery devices. Devices were prepared by compression molding of these nanoscale structures with drugs. This compression molding resulted in strong, dense devices with high uniformity and reproducibility.

The disintegration time and the release of the incorporated drug in buffer solutions was slower than the compression molded devices of the corresponding regular polymers. The regular polymer powders are difficult to obtain and their properties are erratic, since they are prepared by precipitation in non-aqueous solvent and grinding at a temperature below the glass transition temperature which provides irregular particle size and shape. The particles formed by stereocomplex formation are of well-defined flat crystallites that are easy to compression mold.

In a typical experiment, disc (10×2 mm) and rod shape (4×10 mm) devices were prepared by mixing the stereocomplex powder of D-PLA and L-PLA (200 mg, Mw=30, 000) with lidocaine (20 mg) and compression molding into discs of 14×2 mm size.

Lidocaine was released constantly for 30 days when placed in buffer solution p H7.4 at 37° C.

EXAMPLE 5

Formulation and Release of Methotrexate (MTX)

Formulations

Formulations: MTX was incorporated in a stereocomplex of D-PLA/L-PLA (Mw=30,000) prepared by precipitation in acetonitrile. The drug in the form of a powder was mixed with the stereocomplex in the form of a powder, and the mixture compression molded to form tablets. Alternatively, the stereocomplex and MTX were dissolved in dichloromethane, and solvent evaporated to yield a fine powder. For comparison, a solution of random amorphic DL-PLA (Mw=30,000) and MTX was evaporated to dryness to yield a clear flexible and strong yellow film which could be formed into a powder through the use of liquid nitrogen.

In a typical experiment, 300 mg of PLA 1:1 stereocomplex was dissolved in dichloromethane. MTX (5% w/w) was added to the solution, and the mixture was vortexed for two minutes. The solvent was evaporated with a nitrogen stream, to yield a very fine powder. DSC analysis of the powder showed a melting point at 222° C. and no peak at between 170 and 180° C., which confirms the existence of PLA stereocomplex. Discs were prepared by compression molding of the MTX—stereocomplex power (100 mg) using a stainless steel mold (internal diameter 10 mm) and a Carver Press at 10 tons. Alternatively, 300 mg of PLA 1:1 stereocomplex fine powder (average particle size 2.2 microns was mixed with MTX (150 mg) and the uniform powder was compressed into tablets of 200 mg each.

Release of MTX

MTX release was conducted in 10 ml of pH 7.4 phosphate buffer at 37° C. with constant shaking of 150 RPM. Both formulations showed a similar MTX release profile. About 30% of the M was constantly released from the PLA stereocomplex for the first 10 days.

EXAMPLE 6

Formulation and Release of LHRH

Leutinizing Hormone Releasing Hormone (LHRH) is a short peptide which is used to treat prostate cancer. LHRH was incorporated into polymer stereocomplex during the formation of the stereocomplex in solution.

Formulations

Several procedures were used:

a. 250 mg of L-PLA (Mw=30,000) and 250 mg of D-PLA Mw=30,000) were added to 70 ml of acetonitrile at 60° C. To this solution 10 mg of LHRH (2% ww) were added and the solution was allowed to mix at 60° C. for three days, while a white precipitate accumulated. The white precipitate was filtered and dried over a vacuum over night; to yield 460 mg of LHRH loaded PLA stereocomplex. The particle size of the powder was in the range of 1 micron. The acetonitrile solution was kept for LHRH analysis.

b. 250 mg of D-PLA and 5 mg of LHRH were dissolved in 10 ml acetonitrile at 60° C. and the reaction allowed to stand for three days. After three days the white precipitate was filtered and dried in vacuum over night; it yielded 230 mg of LHRH-DPLA stereocomplex. The acetonitrile solution was kept for LHRH analysis.

c. 250 mg of L-PLA (Mw=2,000) and 250 mg of D-PLA (Mw=30,000) were added to 70 ml of acetonitrile at 60° C. To this solution, 50 mg of LHRH were added; and the solution was allowed to mix at 60° C. for one day while a white precipitate accumulated. The white precipitate was filtered and dried over a vacuum over night; it yielded 460 mg of LHRH loaded PLA stereocomplex. The average particle size of the powder was 2.4 microns, and the particles were in the shape of discs. The acetonitrile solution was kept for LHRH analysis.

d. 50 mg of L-PLA (Mw=30,000) and 250 mg of D-PLA (Mw=30,000) were added to 70 ml of acetonitrile at 60° C. To this solution, 30 mg of LHRH were added, and the solution was allowed to mix at 60° C. for one day while a white precipitate accumulated. The white precipitate was filtered and dried over a vacuum over night; it yielded 460 mg of LHRH loaded PLA stereocomplex.

e. 250 mg of L-PLA (Mw=2,000) and 250 mg of D-PLA (Mw=3,000) were added to 70 ml of acetonitrile at 60° C. To this solution, 50 mg of LHRH were added, and the solution was allowed to mix at 60° C. for one day while a white precipitate accumulated. The white precipitate was filtered and analyzed and the release was determined.

Release of LHRH from Formulations

The analysis of LHRH was conducted using the following HPLC method: Mobile phase comprised 30% acetonitrile, 70% TEAP (triethylammoniumphosphate) buffer 0.0M pH-3. Column comprised Lichrosphere RP-18 5 mm (MERCK); Detector. UV 278 nm and flow rate at 1 ml/min.

All samples were filtered through a $2\mu$ filter. One drop of phosphoric acid was added to the sample solutions before injection. The retention time for LHRH was 6.5 minutes and a calibration curve was generated (r2=0.999).

The LHRH content in the acetonitrile solutions (which were saved from the stereocomplexation reactions) was determined in the following manner: 3 ml of the acetonitrile solution (from the procedures described above) were evaporated to dryness and the residue was dissolved in 2 ml of phosphate buffer. LHRH concentration in these solutions was determined by the HPLC method described above. No LHRH peak was shown on the chromatograms for solutions a to e, while more than 80% of the LHRH was found in the solution of formulation f, and the precipitate was almost pure LHRH. LHRH release:

Since the powder of the LHRH in the stereocomplex is very thin, all the attempts to sink it at the release medium failed. The release was conducted in the following way: 100 mg of the powder in 5 ml phosphate buffer were added to a 10 ml syringe. The edge of the syringe was sealed and constantly shaken at a rate of 150 RPM and a temperature of 37° C. At each interval of time, the syringe was inverted so that the solid floated at the top of the buffer and all of the buffer was pushed out of the syringe in a dropwise fashion. Using this technique, the powders of LHRH in PLA stereocomplex (formulations a-e) were analyzed against a control blank of PLA stereocomplex (no drug).

LHRH was constantly released from these powders for a period of about three months with a similar release profile for formulations a and b. No LHRH was detected in the blank polymer. Formulation e, prepared from low molecular weight PLA, released the drug faster, within 30 to 40 days, than the other formulations. The rod formulations released the LHRH for longer time periods than their respective powder formulations.

Block copolymers of D-PLA-co-PGA (PGA= polyglycolic acid, Mw=20,000 at a ratio of 1:1) were stereocomplexed with L-PLA or L-PLA-co-PGA in the presence of LHRH.

Stereocomplexes were formed between D-PLA-b-PEG and L-PLA-b-PEG in various solvents. Nanosize complexes were formed between LHRH with D-PLA by simple precipitation in hot acetonitrile. LHRH was constantly released for over 3 weeks from these nanospheres.

EXAMPLE 7

Formulation and Release of Antisense

Formulation of Antisense

The oligonucleotide ISIS3521 was incorporated into the stereocomplexes in one of the three ways described for LHRH.

TABLE 3

ISIS stereocomplexes composites.

| | L-PLA | D-PLA | DL-PLA | antisense ISIS | Acetonitrile |
|---|---|---|---|---|---|
| a | 125 mg | 125 mg | — | 5 mg | 10 ml |
| b | — | 250 mg | — | 5 mg | 10 ml |
| c | — | — | 250 mg | 5 mg | 10 ml |

After 72 hours the reactions (a, b and c) were stopped and the following results were observed:

a. 220 mg precipitate was obtained; the acetonitrile was kept for analysis of oligonucleotide.
b. Turbid solution was obtained. After 24 hours at 0° C., a white precipitate was obtained. After filtration, 150 mg of solid was collected; the acetonitrile was kept for analysis of oligonucleotide.
c. Clear solution was obtained. After 24 hours at 0° C., small amount of precipitate was obtained.

After acetonitrile evaporation and re-dissolving in phosphate buffer pH7.4.I, ISIS3521 concentration in the acetonitrile solutions was determined by UV absorption at 260 nm.

Release of ISIS

For reaction a, 0.04 mg of ISIS 3521 was detected, which is less than 1% of the initial amount added. The acetonitrile phase from reaction b did not contain ISIS at all and the small precipitate from reaction c was 100% ISIS3521.

In vitro release in phosphate buffer pH7.4 at 37° C. showed a constant release for 5 weeks from formulations a and b.

EXAMPLE 8

Formulation and Release of TRH

TRH is a tripeptide with the following structure: pL-Glu-L-His-L-Pro__NH2. 250 mg of D-PLA (Mw=30,000 or Mw=6,000) were mixed with 25 mg (10% w/w) of TRH in 10 ml acetonitrile at 60° C. The solution became clear after 15 minutes and remained clear for 72 hours, at which point precipitate formed. The solution was very turbid, but could not be filtered at room temperature due to the fine particle size of the precipitate. After cooling at 0° C. over night, the precipitate was filtered. The TRH concentration in the acetonitrile solution and in the powder was analyzed as described above using the Lowry method for peptide analysis. Over 90% of the drug was determined to be in the powder and a negligible amount of the drug was found in the acetonitrile solution. When dispersed in phosphate buffer pH7.4 at 37° C., TRH was constantly released for 6 weeks.

EXAMPLE 9

Formulation and Release of Albumin

Human serum albumin (HSA, 100 mg) was stereocomplexed at 60° C. for 48 hours with a mixture of D-PLA (1 g, Mw=6,000) and L-PLA (1 g, Mw=6,000) or with D-PLA (2 g, Mw=6,000) or with DL-PLA in dioxane (50 ml). A precipitate was obtained for the D-PLA/L-PLA mixture and for the D-PLA solution while very little precipitate was detected for the DL-PLA solution. Accordingly, as determined by the Nynhidrin method for peptide and protein analysis, less than 5% of the HSA was detected in the acetonitrile solutions of the enantiomeric polymers, while most albumin was found in the acetonitrile solution of DL-PLA The precipitates were dispersed in phosphate buffer (pH 7.4) at 37° C. HAS was constantly released from the precipitates for 6 weeks.

EXAMPLE 10

Formulation and Release of Drug from Albumin Stereocomplex

The precipitate of D-PLA-HSA prepared as described in Example 9 was also used as a matrix carrier for the delivery of small drugs. In a typical experiment, a fine powder of ibuprofen (100 mg) was mixed with the D-PLA-HSA or D-PLA-L-PLA-HSA (500 mg) and the powder was compressed into tablets of 300 mg each. The tablets released the ibuprofen for one week when placed in phosphate buffer at physiological pH 37° C. In similar experiments, other proteins were stereocomplexed with PLA enantiomers including fibrin, fibrinogen, collagen and gelatin.

EXAMPLE 11

Formulation of Drug-PLA-PEG copolymer Stereocomplexes

The self assembling of the AB block copolymers poly(L-lactide)-b-poly(ethyleneglycol) (L-PLA-b-PEG) and poly (D-lactide)-b-poly(ethyleneglycol) (D-PLA-b-PEG) in solution in the presence of a bioactive molecule by the racemic packing of enantiomorphic PLA-blocks was studied. AFM studies identified unique self-assembled structures, like rods and coiled coils, with dimensions of several micrometers, for the chiral or racemic PLA packing. The formation of the supra-structures is related strongly to the crystallization of both blocks. The combination of the self organization of a block copolymer in a low molecular weight solvent with the crystallization of both blocks and especially the racemic crystallization of enantiomorphic PLA-blocks offers a new access to isolatable finite block copolymer structures with interesting properties for pharmaceutical applications.

Three representative bioactive molecules, ISIS (an antisense oligonucleotide), LHRH, and methotrexate were incorporated into the polymers either during the crystallization and complex formation, or by mixing the blank stereocomplex particles with the drug and compressing the powder into tablets.

For incorporation of drug during complex formation, LHRH powder (33 mg) was dissolved in acetonitrile solution of L-PLA-b-PEG and D-PLA-b-PEG (100 mg each polymer, Mw=7,000, and PEG Mw=2,000) or into a solution of D-PLA-b-PEG. The solution was allowed to mix at 37° C. over night to form a white precipitate which was separated by filtration. The particles were of a disc shape with an average particle size of between 1 and 3 microns. Analysis of the drug content in the solution and the precipitate showed an encapsulation yield of over 80%. Methotrexate was encapsulated in poor yield by this method.

In a second experiment, the L-PLA-b-PEG/D-PLA-b-PEG stereocomplexes were compression molded into tablets. The relatively uniform small particle size and the unique particle morphology and structures makes this polymer powder very attractive for compression molding devices.

EXAMPLE 12

Formulation of Ibuprofen Stereocomplex

Ibuprofen contains a chiral center and can be obtained in one of the following configurations: 'R', 'S', and 'RS' racemic mixture. It was determined whether ibuprofen will create a stereocomplex with PLA. The reaction was conducted in acetonitrile at 60° C. L-PLA (250 mg, Mw=30,000 or Mw=6,000) were mixed with 25 mg (10% w/w) of one of the three isomers of ibuprofen. After three days, the solutions remained clear. An additional 225 mg of ibuprofen were added and the solutions were allowed to react for another 72 hours and still remained clear. The reaction was stopped, cooled at 0° C. overnight, and the precipitate was filtered.

Ibuprofen concentration in the acetonitrile solution was determined by UV at 254 nm. It was found that over 95% of the drug was in the acetonitrile solution, which indicates no complex formation occurred for any of the ibuprofen isomers. In a similar experiment, L-phenylalanine was reacted with D-PLA or a mixture of D-PLA and L-PLA in acetonitrile, and no complex was formed. These experiments indicate that low molecular weight enantiomers (below 300 daltons) do not form stereocomplexes with the polymers.

EXAMPLE 13

In Vitro and In Vivo Evaluation of Leuprolide-polymer Stereocomplex

Formulations

Preparation of complex: Solutions of leuprolide acetate in acetonitrile (4 mg) and D-PLA, (58 mg, Mw=100,000) and L-PLA (38 mg, Mw=30,000) in acetonitrile were mixed together (total 5 ml) and allowed to stir for 3 days at 50° C. The precipitated powder was isolated by filtration to yield 98 mg of 1 micron size porous particles. No leuprolide remained in the acetonitrile solution.

Release

In vitro release was conducted in phosphate buffer pH 7.4 at 37° C. Leuprolide concentration was determined by HPLC (acetonitrile:water, C18 column, 1 ml/min). About 37% of the drug was released constantly in 40 days.

Complex powder containing 13% leuprolide was prepared in a similar manner. These powder formulations were used for in vivo study in rats. 17 Sabra rats (250 g) were divided into 3 groups, 5 injected with saline solution, 5 injected with 5 mg/kg leuprolide-dose in 4% polymer formulation and 5 injected with 5 mg/kg leuprolide-dose in 13% polymer formulation. Two rats were injected with the blank polymer (50 mg/kg). Blood was taken at predetermined time points and the testosterone blood levels was determined by a standard kit for the determination of testosterone in human blood. As demonstrated, testosterone levels remained low for the 40 days of the study which is similar to the data obtained for the clinically used formulation, Lupron, as described in the literature. This experiment demonstrates the effectiveness of then use of these stereocomplexes for peptide delivery.

EXAMPLE 14

Stereoselective Polymers with Cationic Residues for Gene Delivery

Synthesis of Polymers a. PEI-D-PLA Polymers

Block copolymers of polyethylenimine and D-PLA are prepared by the attachment of poly(D-lactic acid on polyethylenimine using DCC as coupling agent. In a typical experiment, short chain polyethylenimine (Mw=600, Polysciences catalog, USA) was added to a chloroformic solution of D-PLA and dicyclohexylcarbodiimide (DCC) and N,N-dimethylamino pyridine (DMAP) (1% per amino groups). The solution was allowed to stir at room temperature for 3 days, filtered to remove the dicyclohexylurea (DCU) by product and the clear solution was extracted with water, dried over $MgSO_4$ and evaporated to dryness. The residue was purified by precipitation in ether:petroleum ether mixture from a concentrated dichloromethane solution. The resulting polymer contain both the D-PLA and PEI as determined by NMR and nitrogen analysis. Copolymers of the ratio PEI: D-PLA ranged from 3:1 to 1:3 are prepared. D-PLA of molecular weights, 2,000, 10,000 are used for these copolymers.

Alternatively, random copolymers are prepared by transamidation reaction between PEI and D-PLA in solution or in melt. In a typical experiment, D-PLA of a molecular weight 55,000 was dissolved in dry dioxane and PEI-600 (2:1 w/w) was added to the solution. The reaction solution was heated to reflux for 5 hours and the solution was added to deionized water solution to precipitate the polymer. The precipitated polymer was dissolved in dichloromethane, dried over $MgSO_4$ and evaporated to dryness. The resulted polymer contained PEI residues as determined by NMR and nitrogen analysis.

b. D-PLA with Carboxylic Acid End Groups

D-PLA with carboxylic acid end groups that can react with amino groups to form amide bonds are prepared by either polycondensation of D-lactic acid (prepared by hydrolysis of the commercially D-lactide available from Purac) in toluene or by partial hydrolysis of poly(lactide) in a base solution or by enzyme cleavage. Low molecular weight PEI are synthesized by acid-catalyzed ring-opening polymerization of aziridine in aqueous solution. Short chain PEI, up to 2,000 Daltons, are preferred for gene delivery as they have shown to be less toxic compared to longer chains [D. Fischer, et al. Eur. J. Cell Biol. 75 (1998) 107; T. Bieber, et al. Eur. J. Cell Biol. 75 (1998) 108].

c. Synthesis of Polylysine-D-PLA Copolymers

Carboxylic acid terminated D-PLA was conjugated to polylysine to form a stereoselective polymer with cationic capacity. The preferred polylysine is of D-configuration and of low molecular weight which is considered as less toxic and easy to being eliminated from the body. The D-configuration will be aligned with the D-PLA and increase the stereocomplexing capacity. The methods for the formation of linear the graft block copolymers of polylysine-PLA are similar to the methods described above for PEI. Random and graft copolymers of D-PLA and lysine can be prepared using the methods described by Langer et al. *Macromolecules*, 28:4736–4739 (1995); *JACS* 115:11010–11011 (1993). The preferred lysine configuration for these copolymers is the D-configuration which forms a uniform D-configuration polymer chain with the D-lactide residues. To obtain AB block copolymers of polylysine-D-PLA, the g-amino side groups of the polylysine are protected by benzoxycarbonyl protecting groups and then attach the D-PLA chain to the free carboxylic end group by an ester bond.

COMPLEXATION WITH DNA

This polymers were complexed with Herring DNA by mixing the DNA and polymer is buffer solutions or mixtures of buffers and acetonitrile or DMSO to form a complex.

Publications cited herein and the material for which they are cited are specifically incorporated by reference. Modifications and variations of the present invention will be obvious to those skilled in the art from the foregoing detailed description and are intended to be encompassed by the following claims.

We claim:

1. A polymeric carrier for delivery of a bioactive or bioreactive molecule, comprising a stereocomplex of at least one biocompatible stereoselective polymer and a bioactive or bioreactive molecule.

2. The polymeric carrier of claim 1 wherein the polymer is selected from the group consisting of linear and branched polyesters, polycarbonates, polyanhydrides, polyhydroxyacids, polyalkylene oxides, proteins or polyamino acids, polysaccharides, and block and copolymers thereof.

3. The polymeric carrier of claim 2 wherein the polymer is selected from the group consisting of D-PLA homo- and block-polymers, linear and branched L-PLA homo- and block-polymers, copolymers thereof and mixtures thereof in stereocomplexed form.

4. The polymeric carrier of claim 1 wherein the bioactive molecule is selected from the group consisting of peptides, proteins, nucleotides, oligonucleotides, sugars, carbohydrates, lipids, and synthetic organic or inorganic drugs.

5. The polymeric carrier of claim 1 wherein the polymer is a stereoselective drug of a molecular weight of 300 daltons or higher.

6. The polymeric carrier of claim 4 wherein the oligonucleotides are selected from the group consisting of antisense, genes, plasmids, and viral vectors.

7. The polymeric carrier of claim 6 wherein the stereoselective polymers are selected from the group of polymers with cationic residues consisting of lysine, polylysine, sperime, spermidine, and polyethyleneimine.

8. The polymeric carrier of claim 4, wherein the bioactive molecule is selected from the group consisting of hormones, clotting factors, proteases, growth factors; and vaccines.

9. The polymeric carrier of claim 1 wherein the bioactive molecule is dispersed or dissolved in the polymeric stereocomplex.

10. A pharmaceutical preparation comprising any of the polymeric carriers of claims 1–9 in a form suitable for administration to a patient in need thereof.

11. The pharmaceutical preparation of claim 10 in a form selected from the group consisting of particles, tablets, pellets, rods, beads, prosthetic implants, ointments, pastes, creams, and gels.

12. The pharmaceutical preparation of claim 10 in a pharmaceutically acceptable carrier and dosage form suitable for administration by parenteral or enteral routes.

13. A method for manufacturing any of the polymeric carriers of claims 1–9 comprising mixing together at least one polymer forming a stereocomplex and bioactive or bioreactive molecules to be incorporated therewith.

14. The method of claim 13 wherein the stereocomplex is formed by precipitation of the polymers in solution.

15. The method of claim 13 wherein the stereocomplexes formed by melting together the polymers forming the stereocomplex.

16. The method of claim 13 wherein the bioactive or bioreactive molecules are incorporated into the stereocomplex at the time of formation.

17. The method of claim 13 wherein the bioactive or bioreactive molecules are dispersed on or bonded to the stereocomplex.

18. A method for administering bioactive or bioreactive molecules to a patient in need thereof comprising administering to the patient an effective amount of the pharmaceutical preparations of claim 10.

19. The method of claim 18 wherein the pharmaceutical preparation is in a form selected from the group consisting of particles, tablets, pellets, rods, beads, prosthetic implants, ointments, pastes, creams, and gels.

20. The method of claim 18 wherein the pharmaceutical preparation is in a pharmaceutically acceptable carrier and dosage form suitable for administration by parenteral or enteral routes.

* * * * *